United States Patent

Xu

Patent Number: 5,813,049
Date of Patent: Sep. 29, 1998

[54] WELDING HELMET

[76] Inventor: Long Xu, 88-45 Eldert La., Woodhaven, N.Y. 11421

[21] Appl. No.: 767,850

[22] Filed: Dec. 17, 1996

[51] Int. Cl.[6] ............................................ A42B 1/00
[52] U.S. Cl. .................................................. 2/8; 2/410
[58] Field of Search ........................................ 2/8, 7, 410

[56] References Cited

U.S. PATENT DOCUMENTS

| | | | |
|---|---|---|---|
| 2,644,161 | 7/1953 | Meyer | 2/8 |
| 3,868,727 | 3/1975 | Paschall | 2/8 |
| 4,646,363 | 3/1987 | Wood | 2/8 |

Primary Examiner—Gloria M. Hale

[57] ABSTRACT

This invention is focused to overcome the common deficiencies in welder's helmets. The welding helmet's view window (Mother Window) consists of two (2) smaller view windows. The upper portion of the mother window [22] is a tiny strip view window [14] which provides a better view for users; the lower portion of the mother window is a shade window for protecting the welder's eyes. In addition, a removable chest protection unit [17] is added to the bottom of the helmet for protecting the welder's upper chest area.

8 Claims, 1 Drawing Sheet

WELDING HELMET

BACKGROUND OF THE INVENTION

Welding helmets presently used in electrode arc welding do not provide a welder with adequate sight to start welding. Without adequate sight a welder has to rely on memory and physical sense of the members. As a result, the welding course will tend to deviate from its course which will lead to poor quality welding. In order to overcome the problem, most welders do not presently wear welding helmets to start the welding. Without a helmet for protection the welding electrode arc can cause serious injury to the welder's eyes.

In addition, the skin of the upper chest area of a welder is usually exposed to air which is potentially dangerous from electrode arc burn during the summer season. This is because welders usually wear light clothing such as t-shirts.

SUMMARY OF THE INVENTION

The welding helmet includes a view window which utilizes uniquely structured mother and son view windows. The mother window consists of two different son view windows. The first son view window is composed of a tiny strip air gap (14) enclosed by two clear transparent glasses and is located at an upper portion of the mother window. Welders can simply move his/her eyeballs to bring the elding members to sight through the tiny strip of view window. The advantage with this type of tiny strip of clear view window is that a welder can precisely locate the members without exposing himself/herself to the harmful electrode arc and ultraviolet rays. A lighting block strip (12) is placed behind the tiny clear transparent window (14) to block any ultraviolet rays that may enter a welder's eyes. The second son view window (13) consists of two clear transparent glasses with a shade glass therebetween. The shade glass functions the same way as the traditional helmet. But, with a clear transparent glass added to the front and back of the shade glass, the shade glass reduces the ultraviolet rays entering the welder's eyes significantly. The second son view window is located at the lower portion of the mother view window and is almost the same size as the mother view window.

In addition, a removable transparent shield, the upper chest protection unit (17) is attached to the helmet botttom for protecting a welders upper chest skin from electrode arc burn during the summer.

DESCRIPTION OF THE PREFERRED EMBODIMENTS

Figures 1, 2:
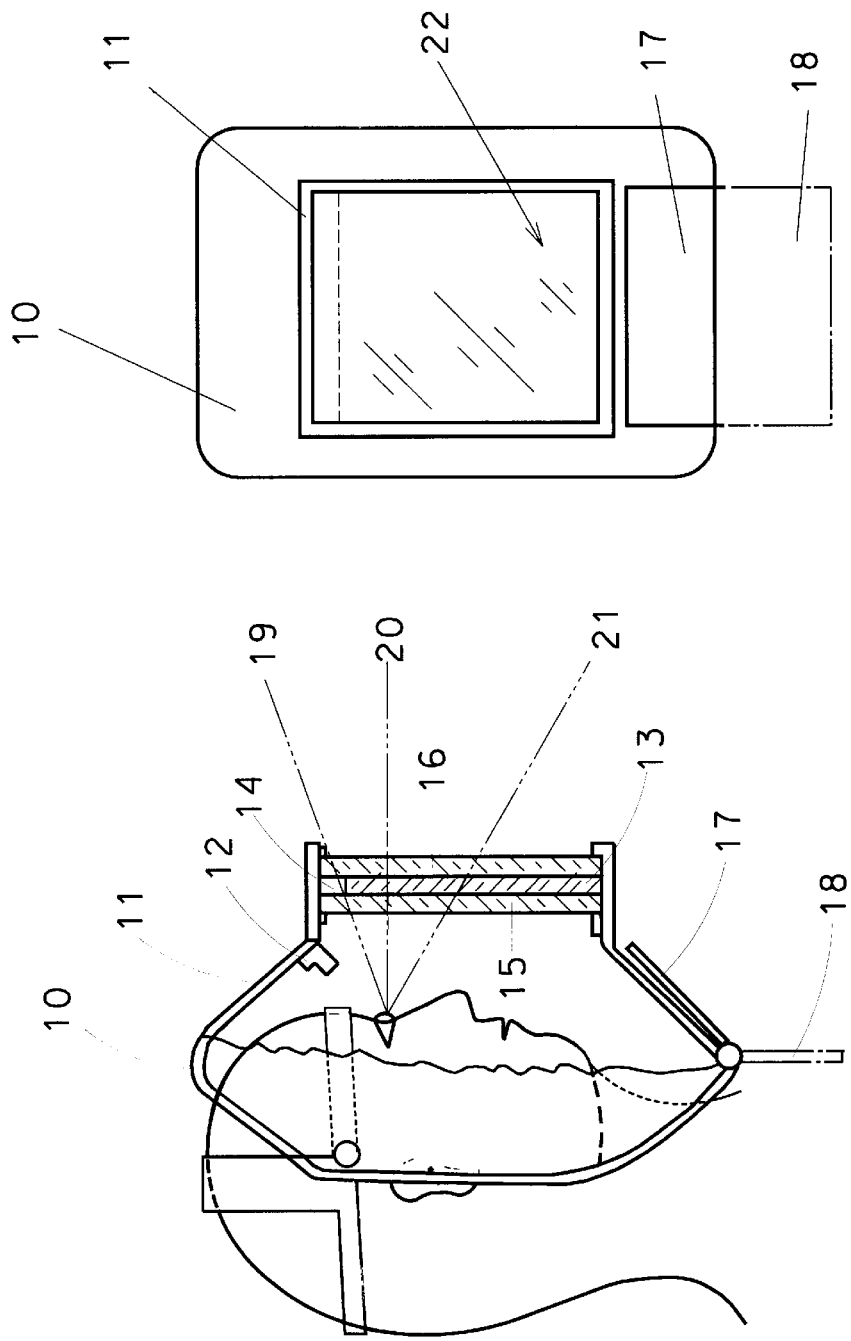
FIG. 1 is a side view and cross section of the invention.
FIG. 2 is a front view of the embodiment shown in FIG. 1.

The basic units from the helmet are shown in FIG. 1. The apparatus (10) mainly consists of a housing unit (11), a mother window (22) and an upper chest protection unit (17).

The housing unit is the same as traditional helmets and is dimensioned to completely cover the user's face and neck and is fabricated from high strength, impact resistant material pivottally attached to the headband. A removable upper chest protection unit (17) is pivotally attached to the bottom of the housing unit and is fabricated from the same material as the housing unit. The mother view window (22) comprises two clear transparent glasses (15) and (16) and a shade glass (13) which is smaller than the clear transparent glasses in height. Thus, a tiny strip of clear view window (14) is formed at the top of the mother window. This tiny strip of clear window is called the first son view window (14). The second son view window comprises one shade glass (13) covered by one clear transparent glass on the front and the back. The clear transparent glasses (15) and (16) function as an ultraviolet ray reduction agent.

A lighting blockage strip (12) is placed behind the first son's view window (14). The lighting blockage strip is usually fabricated from light absorbing black material or the like. The upper vision sight path of a welder (19) for starting the welding; the level vision sight path (20) and the lower vision sight path (21) utilized by the welder during welding are shown in FIG. 1.

I claim:

1. A welding helmet comprising:

a housing unit configured to completely cover a user's face and neck;

a headband attached to the housing unit for attaching the helmet to the user's head;

said headband pivots from said housing unit for ease in donning and removing the helmet from the user's head:

said housing unit includes a mother view window constructed of two clear transparent glasses and a shade glass therebetween;

said shade glass between said two transparent glasses is shorter in length that said two transparent glasses thereby forming a clear first son view window at the top of the mother window and a second son view window below said first son view window.

2. A welding helmet as claimed in claim 1 and further including a lighting blockage strip attached to the housing unit at the upper view window for blocking any ultraviolet rays from a user's eyes that may enter therethrough.

3. A welding helmet as claimed in claim 1 and further including a removable upper chest protection unit pivotally attached to the bottom of the housing unit for protecting the upper chest of the user.

4. A welding helmet as claimed in claim 2 and further including a removable upper chest protection unit pivotally attached to the bottom of the housing unit for protecting the upper chest of the user.

5. A welding helmet as claimed in claim 1 wherein said housing unit is constructed of a high strength, impact resistant material.

6. A welding helmet as claimed in claim 2 wherein said housing unit is constructed of a high strength, impact resistant material.

7. A welding helmet as claimed in claim 4 wherein said housing unit and said removable upper chest protection unit are constructed of a high strength, impact resistant material.

8. A welding helmet as claimed in claim 3 wherein said housing unit and said removable upper chest protection unit are constructed of a high strength, impact resistant material.

* * * * *